United States Patent
Gehl

(12) 
(10) Patent No.: US 6,811,570 B1
(45) Date of Patent: Nov. 2, 2004

(54) IMPLANT MADE OF A REABSORBABLE CERAMIC MATERIAL

(75) Inventor: Gerolf Gehl, Kusnacht (CH)

(73) Assignee: Augmentec AG, Langenaltheim (DE)

(*) Notice: Subject to any disclaimer, the term of this patent is extended or adjusted under 35 U.S.C. 154(b) by 0 days.

(21) Appl. No.: 09/529,897

(22) PCT Filed: Oct. 19, 1998

(86) PCT No.: PCT/EP98/06599

§ 371 (c)(1),
(2), (4) Date: Nov. 30, 2001

(87) PCT Pub. No.: WO99/20319

PCT Pub. Date: Apr. 29, 1999

(30) Foreign Application Priority Data

| Oct. 21, 1997 | (DE) | 197 46 467 |
| Jan. 16, 1998 | (DE) | 198 01 428 |
| Feb. 5, 1998 | (DE) | 198 04 520 |
| Aug. 14, 1998 | (DE) | 198 36 985 |

(51) Int. Cl.$^7$ .............................. A61F 2/02; A61F 2/12
(52) U.S. Cl. ........................ 623/23.75; 623/8
(58) Field of Search ............... 623/8, 11.11, 16.11, 623/23.56, 23.57, 23.58, 23.6, 23.61, 23.64, 23.72, 23.73, 23.74, 23.75; 435/284, 240; 424/422, 423, 424; 423/305, 306, 307

(56) References Cited

U.S. PATENT DOCUMENTS

| 5,149,368 A | 9/1992 | Liu et al. |
| 5,306,303 A | 4/1994 | Lynch |
| 5,324,294 A | 6/1994 | Elia et al. |
| 5,462,722 A | 10/1995 | Liu et al. |
| 5,571,182 A | 11/1996 | Ersek et al. |
| 5,922,025 A * | 7/1999 | Hubbard ..................... 623/8 |
| 6,544,290 B1 * | 4/2003 | Lee et al. ............... 623/23.63 |

FOREIGN PATENT DOCUMENTS

| EP | 1 047 459 B 1 | 10/1998 | |
| WO | WO 93/15721 | 2/1993 | |
| WO | WO 94/04657 | 8/1993 | |
| WO | WO 96/39202 | 6/1996 | |
| WO | WO 96/39202 | * 12/1996 | .............. 623/16.11 |

OTHER PUBLICATIONS

Jürgen Vogël and Peter Wange, "Phosphate Glasses and Glass–Ceramics for Medical Applications", Glastech Ber. Glass Sci. Technol. vol. 70, No. 7 (1997), pp. 220–223.

Jing Jing Qian and Rajendra S. Bhatnagar, "Enhanced Cell Attachment to Anorganic Bone Mineral in the Presence of a Synthetic Peptide Related to Collagen", Journal of Biomedical Materials Research, vol. 31 (1996), pp. 545–554.

Werner Vogel and Wolfram Höland, "The development of Bioglass Cerqmics for Medical Applications," Angnew.Chem.Int.Ed.Engl. 26 (1997). Pp. 527–544.

J. Vogel, K.J. Schulze, D. Reif, P. Hartmann, U. Platzbecker and B. Leuner, "Resorbable porous phosphate invert glasses—first in vitro and in vivo results," Bioceramics, vol. 10 (1997), pp. 57–61.

* cited by examiner

*Primary Examiner*—David J. Isabella
(74) *Attorney, Agent, or Firm*—Reed Smith LLP; Stanley P. Fisher, Esq.; Juan Carlos A. Marquez, Esq.

(57) ABSTRACT

The invention relates to an implant, especially a breast implant, which is made of a biocompatible material with a pore structure. The biocompatible material is preferably designed to be reabsorbable.

9 Claims, 2 Drawing Sheets

IMPLANT MADE OF A REABSORBABLE CERAMIC MATERIAL

BACKGROUND OF THE INVENTION

1. Field of the Invention

The invention relates to an implant more particularly suitable for use as a breast implant.

2. Description of the Related Art

Implants such as epitheses for the compensation of congenital or acquired bodily defects have long been known in surgery and have been described on many occasions. Epitheses are individually modeled organ replacements of materials, which are more particularly employed for covering facial defects including those of the ears, and however also for functional applications in prosthetics. Implants are natural or artificial and generally permanent shaped parts, which are incorporated in the body as a plastic replacement or for mechanical reinforcement, as for example eyeball epitheses.

Implants and epitheses are frequently employed to mask the effect of accidents or of surgical operations and to simulate the natural condition of the body. A frequent application is the simulation or enlargement of the female breast, as for instance to compensate for natural defects or deficiencies or after surgical amputation due to malignant tumors. Further fields of application are the compensation of congenital defects or defects due to injury or to an operation on the head.

Implants in the form of silicone-filled cushions have become familiar more particularly in aesthetic breast surgery. Implants are often employed for the replacement or stabilization of bones or parts thereof.

In the intermediate field between epitheses and implants it is frequently a question of covering over a defective superficial part of the body, as for example for aiding the healing of wounds and for the improvement of hygiene. Here protheses do not however always constitute the best solution to existing problems. A basic disadvantage of epitheses is that they are only capable of compensating for a defect of the body in appearance and forever remain a foreign body.

As seen from these points of view systems would be desirable capable of closing a wound remaining after an operation or injury or of filling a body cavity, which has been, produced, while simultaneously rendering possible the invasion by body tissue. It is in this manner that a complete integration of an implant into the body could be achieved. In an ideal case the remodelling of contours of the body would be consequently possible to reform body contours with a model shape.

Furthermore it would be desirable to make available implants which are so configured and treated and of such a texture structure that they favor the ingrowth of body tissue into the interior. Furthermore more especially in the field of aesthetic breast surgery it would be desirable, for an implant simulating the breast to be slowly resorbed during and/or after the invasion of body tissue from the body so that its place is completely assumed the by body tissue.

SUMMARY OF THE INVENTION

One object of the invention is to create an implant which avoids the above described disadvantages of conventional epitheses and implants while nevertheless being safe from a medical point of view and furthermore being tissue-compatible. The implant is to maintain its dimensional stability during the time it functions and is to have such a structure that invasion or ingrowth of body tissue may take place and an at least partial resorption is possible.

This object is to be attained with an implant which comprises a body-compatible ceramic material able to be resorbed by the body and having a pore structure.

DESCRIPTION OF THE PREFERRED EMBODIMENTS

Figure 1:
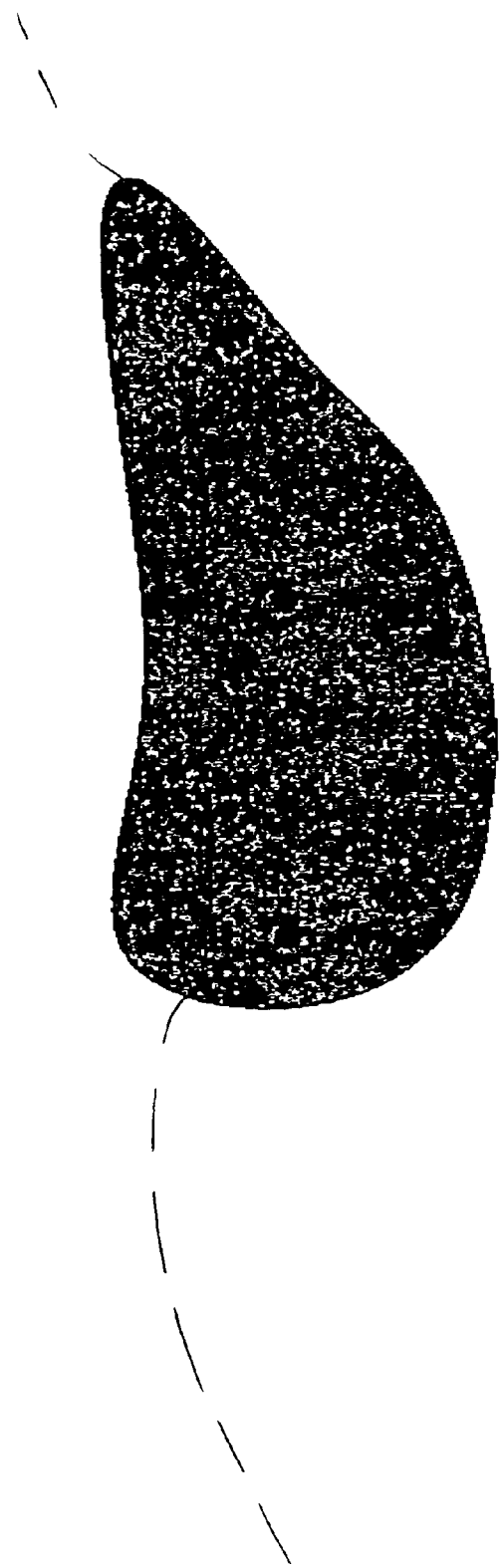
FIG. 1 shows a female breast implant with a porous structure according to one embodiment of the invention.

The implant comprise a body-compatible material. Body-compatible means more particularly tissue-compatible in the sense that an invasion of body tissue may take place into the implant. The material is to more particularly encourage vascularization, this being one of the essentials for resorbability by the body and the invasion of body tissue.

The term pore structure is employed herein in the sense of a spongiform, foam or honeycomb structure, that is to say every structure which is provided with irregularly or regularly formed cavities. It is in this manner that it is not only possible to keep the weight of the implant low, but also to facilitate vascularization and the invasion by body tissue. Dependent on the particular purpose it is possible for the material of the implant to consist of hard or less hard materials. Thus it is convenient for example, for the simulating the nose, eye, ear and parts thereof to employ a more rigid material, which for instance may consist of hydroxlapatite. Dependent of the purpose of the application it is convenient to employ a material more resistant to resorption or of a material which is fairly rapidly resorbed in the body. More particularly in the case of breast implants it is appropriate to use a material able to be resorbed in the body so that gradual and complete displacement may take place.

One preferred material for the implant in accordance with the invention is glass ceramic, calcium phosphate ceramic and more especially tricalcium phosphate and hydroxylapatite, which all possess the necessary porous on spongiform structure and consequently render possible the ingrowth of body tissue. The spongiform, resorbable hydroxylapatite is available from the Fratec Company of Mannheim, Germany.

The materials possess the advantage that in the initial phase, i. e. after implantation, they form a solid porous foundation structure, which remains stable for prolonged periods of time. After successful invasion by the body tissue and vascularization therein an accelerated digestion or, respectively, resorption takes place from the inside, which removes the supporting foundation and provides space for the ingress of body dells.

A further "ceramic" material coming into question is plaster. The term plaster is employed herein in the sense of calcium sulfate dihydrate, that is to say plaster in the hydrated and set form. By the addition of a suitable foam forming agent, moldings with coarse pores can be manufactured. The material possesses the advantage that it may be, extremely readily shaped by molding and milling and may be adapted to the intended purpose of use, that is to say filling a cavity of the body after injury or after an operation.

Accordingly the invention also contemplates an implant of a prepared, shaped part, preferably of plaster.

Glass ceramic possesses the same advantage of being able to be milled and has already been tested in medicine as a bone substitute. Materials with a greater or lesser biosolubility are known. Glass ceramics are fully body-compatible and are, dependent on formulation, completely resorbed in the course of time lasting between a few months and several years. Such materials are for example described in J. Vogel et al., Bioceramics, 1997, 57; Angew. Chem. Int. Ed. Engl. 26 (1987), 527; and Glastech. Bir. Classci.technol.70 (1997), 220, which is incorporated herein by reference. Spongiform (i.e., resembling a sponge; soft and porous; porous) glass ceramic is for example supplied by the Biovision Company of Illmenau, Germany with the designation Bioverit®. See also the German patent publication 19,614, 421 A1, which is incorporated herein by reference, which relates to a polymer bound bone substitute material, along with the above-mentioned materials to be modified according to the invention for making soft tissue implants.

For the design of the implants more particularly for use in the thoracic region it is an advantage to provide a configuration, in which a generally hemispherical implant comprises a readily resorbed core and a slowly resorbed external half shell. The core accordingly is exposed on the body side and will be more rapidly resorbed than the protective and supporting half shell.

In order to promote the ingrowth of body tissue it is convenient to provide the implant with a casing or coating, which promotes the ingrowth of the implant into the body and the formation of tissue in the implant. Such a casing or coating may advantageously consist of keratinocytes as same are inherently known for the treatment and closure of burn injuries. It is however possible to employ collagen or materials, which promote the formation of binding of collagen to body cells. In this case natural or synthetic proteins come into question as being similar are for forming binding to body cells according to the invention. Examples of such proteins are known for instance in the patent publications WO-A-91/02537, WO-A-93/11781 and J. J. Qian and R. S. Bahtnagar in J. Biomed. Mater. Res. 31, 545 (1996), which are all incorporated herein by reference.

As already described, glass ceramic is a material which is particularly preferred in the invention. This material possesses a pore structure and is available particularly in the form of a part pre-shaped by milling and/or casting in a mold.

Glass ceramic implants in accordance with the invention are sintered in a mold in an inherently known method starting with phosphate glass granules. The sintering temperature will generally be between 600 and 800 degrees C., this leading to a superficial fusion and sintering of the granules. Simultaneously during such sintering operation there is a partial crystallization.The grain size of the granules will preferably be in a range of 200 to 500 $\mu$m. The chemical composition of a phosphate glass employed for this purpose will for example amount to 32.6 mol % $P_2O_5$, 27.6 mol % CaO, 27.6 mol % $Na_2O$ and 12.2 mol % MgO. The $Na_2O$ content may be completely or partly replaced by $K_2O$. After sintering such materials may for example have a fraction of open pores equal to 65%, the pore diameters being to an overwhelming extent in a range of 150 $\mu$m to 400 $\mu$m.

The phosphate glass or, respectively, the implants may be set to a desired pH value by suitable doping with alkali ions. This value can on the one hand be within the physiological range and on the other hand may also be in the basic range, as for example between pH 7.7 and 8.7, and preferably in a pH range of 7.9 and pH 8.4. It is known that tumors shift the normally neutral to slightly basic medium of cellular tissue into the acidic range and thus create a medium or environment promoting tumor growth. An implant, which is charged with ions increasing basicity and more particularly alkali metal and alkaline earth metal ions, is able to oppose such shift into an acid range. Following tumor surgery for removing tissue parts, a basic formulation of the implant used for correction may be advisable.

The implants in accordance with the invention may as a complementary measure be charged with medicaments, more especially with antibiotics, cytostatics and the like, incorporation by embedding more particularly coming into question, which ensures a continuous or phased release as part of resorption of the implant. The employment of the implants purely as medicament vehicles for the treatment of disease processes by the successive release of the active substance or substances is also a possibility to be considered, resorbability of the implant being preferred but not being necessary in every case. The latter possibility assumes later explantation.

The implants in accordance with the invention are more particularly suitable as wound closure means, that is to say for direct placement on or in the open wound, something which renders possible and promotes the ingrowth of tissue. All implants in accordance with the invention render possible obtaining volume to a degree, which would otherwise not be possible. Implants of hard mineral material are for instance glass ceramic or hydroxylapatite and furthermore offer a supporting function in the time before the minerals are substantially resorbed.

For applications in the aesthetic and cosmetic fields, as for instance enlarging the breast, in the case of the employment of glass ceramic there is the particular advantage that adhesion of the scare tissue is substantially avoided and tissue degradation do not occur.

Figure 2:
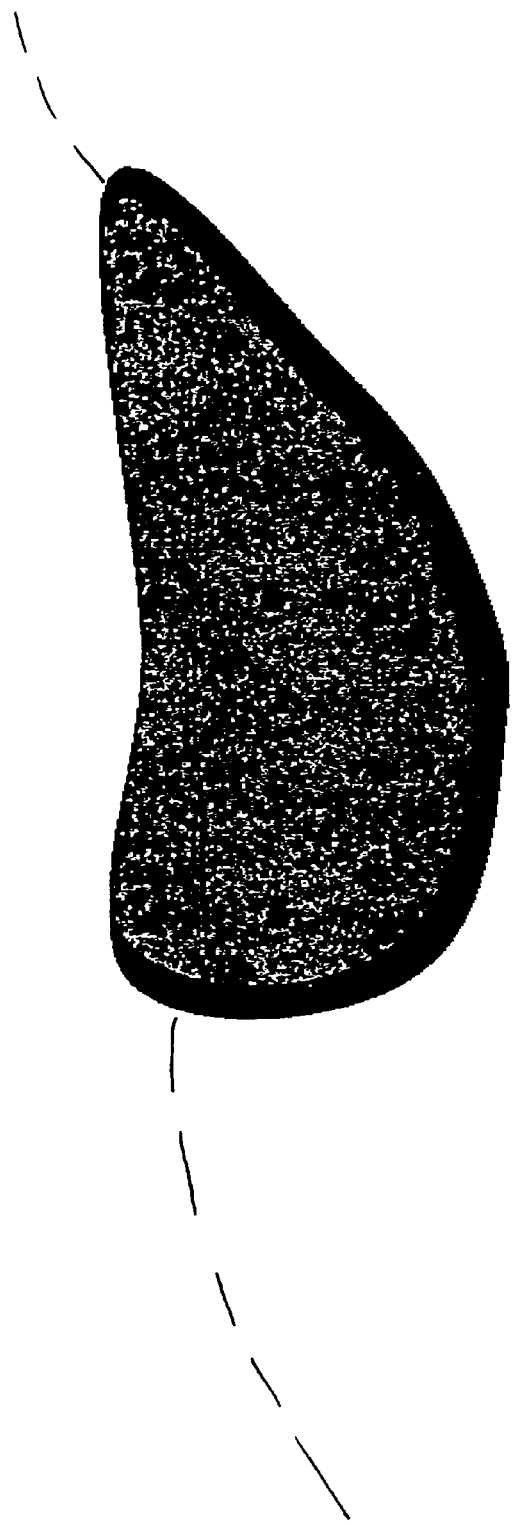
FIG. 2 shows a female breast implant with a rapidly resorbed core and a slowly resorbed external shell according to another embodiment of the invention.

FIG. 1 shows a female breast implant with a porous structure according to one embodiment of the invention, while FIG. 2 shows a female breast implant with a rapidly resorbed core and a slowly resorbed external shell according to another embodiment of the invention.

It may be more particularly be an advantage to not only provide the pre-shaped implants with a coating or impregnation promoting invasion of cells, but in a complementary or alternative manner to incorporate cells in the implant and to cultivate the cells so introduced in a conventional nutrient solution. The incorporation of cells may for example also be performed by adding cells to a nutrient solution and placing the implant in the nutrient solution, the cells then being drawn into the cavities by capillary action. The cells may be cells foreign to the body, which are compatible with the tissue of the implant recipient or however of cells from the implant recipient, in the case of a breast implant for example of cells from the breast obtained. Fat cells are preferred, to which if appropriate, antioxidants are added for stabilization, or human cartilage cells as well may be added. Cell materials may for example be obtained from the Geistlich Company of Luzern, Switzerland (http://www.geistlich.ch/biomaterials/en/) and Maerz, Germany. The cells are best grown for this special application and cultivated in the nutrient solution. There are simply too numerous natural or synthetic proteins or cell materials available from the suppliers to be listed inclusively in the specification. As such, preferred examples are given as follows: collagen, synthetic peptides enhancing cell binding which mimic active segments of collagen, cell surface receptors for collagen and fibronectin, growth inducing peptides, fat cells, human cartilage cells and keratinocytes.

A method for the production of plaster implants with embedded cells and more especially of fat cells is such that the plaster employed for shaping is agitated with a suspension of such cells in a suitable medium and is allowed to set in the desired form or mold. It will be clear that the plaster in powder form used for this should be sterile. The molding or form so produced can be deep frozen after setting. After thawing it is possible for the implant then to be shaped by milling to the desired size. Owing to the pore structure of the plaster a rapid penetration of blood is ensured after implantation and consequently also of supply of nutrients to the cells. The cells then have the possibility of reproduction and expansion in the course of resorption of the plaster matrix by the body. Glass ceramics are best impregnated with a cell suspension.

In practice the method is so performed that in the case of a partial excision, performed in tumor surgery, of a female breast on account of a tumor the pre-shaped, coated and possibly cell charged implant is introduced directly into the wound and the wound is then closed again. In order to ensure and to promote the supply of blood to the implant it is possible to produce an anastomosis between the remaining, healthy breast and the implant bearing breast. The anastomosis improves not only the establishment of the blood supply but also the nutrition of embedded body fat cells from the healthy breast and accordingly invasion of body tissue into the implant.

The implants in accordance with the invention are particularly suitable for substitution in cosmetic operations on the female breast. As part of measures for enlarging the breast for cosmetic reasons, but also however for gender reassignment surgery the implants of the invention may be used with advantage. As a rule the procedure will be that firstly using a so-called tissue expander the skin is stretched as may be necessary. After the conclusion of stretching the operation as such is performed in which the implant is introduced and is anchored in the breast. The implants firstly serve to ensure the correct configuration and stabilization of the predetermined form. Pari passu with the dissolution of the implant and its replacement by tissue the supporting function is taken over by the newly formed tissue.

The reconstruction of extensive facial defects following loss of bones and soft tissues is rendered possible using ceramic structures of different density and resorption rates. For instance in the case of a major facial defect (for example owing to an operation cavity following the removal of a tumor) it is possible to insert a pre-shaped implant block, which already contains determining means for bone and soft tissue substitution. Such implant blocks may also be shaped freehand by an artist or under the control of a computer (stereolithographically) so that the structures, which are to ossify and the preliminary stage of the soft tissue are already stored by special determinative charging in the implant material.

In a similar fashion bone and soft tissue defects in the crural region or in other regions of the body can be treated as well.

The implant material can be adapted to suit the respectively desired resorption rate by suitable modification of its composition, density, porosity and configuration.

The implant in accordance with the invention may in a similar method be employed for organ substitution (as for example liver and pancreas). Following partial resection of the liver for example, a coarse pored ceramic implant is introduced with a wild card function, which is charged with liver-specific cells or which is correspondingly impregnated or encoded with peptide compounds or growth inducing agents. The hard implant is best composed of a more readily resorbing core and a less readily resorbing casing, which is only completely resorbed after dissolution of the core. This ensures that space is held available until spreading of the function-specific cells is completed. Following further colonization and filling with the organ cells (in about 3 to 4 months) there will be the complete resorption of the supporting structures so that in the final state soft, function-specific tissue occupies the site. In a corresponding manner it is possible for the entire organ to be substituted in several stages for which purpose several operation and healing phases for corresponding segments are necessary.

In a similar manner it is possible for teeth to be replaced. However in this case the non-resorbable ceramic implant is employed as the tooth or bone substitution means. may be required, for instance directly after the extraction of a tooth, the implant is introduced into the suitably prepare alveolus. At the interface it is suitably encoded for adhesion to the recipient's own bone material, there being an ingrowth and to a certain degree an exchange of the implant material The implants in accordance with the invention may be employed for the correction of the appearance of the female breast in particular both after surgical removal of tissue due to a disease process and also following accidents and ensuing loss of tissue in order to achieve a better contour, for example of the legs or of the podex, or also for correction of contours after the loss of parts of the cheeks, the nose the eyes or the ears or, respectively, owing to a congenital absence of such the parts.

What is claimed is:

1. An implant for adding or restoring a human soft tissue, comprising a shell and a core covered by the shell, the core and the shell being made of a soft tissue-compatible glass ceramic material with a porous structure formed to facilitate vascularization and ingrowth of the human soft tissue, said material consisting of sintered phosphate glass granules with a grain size of 200–500 $\mu$m and being resorbable by a body, wherein the core is formed to be resorbed faster than the shell by the body.

2. The implant according to claim 1, wherein the implant is pre-shaped in a form of a body part.

3. The implant according to claim 1, further comprising a coating of keratinocytes, collagen or a material which promotes collagen formation on body cells.

4. The implant according to claim 3, wherein the coating is composed of a natural or a synthetic peptide.

5. The implant according to claim 1, wherein the glass ceramic material is set to a pH value between 7.7 and 8.7.

6. The implant as claimed in claim 5, wherein the implant is preshaped and modifiable and adaptable by removing a portion of the glass ceramic material therefrom.

7. The implant as claimed in claim 6, wherein the implant is impregnated with viable cells.

8. The implant as claimed in claim 7, wherein the implant is precultivated in a cell-containing nutrient solution.

9. The implant as claimed in claim 1, wherein the implant is used for the restoration or enlargement of a breast.

* * * * *